(12) United States Patent
Shepherd

(10) Patent No.: US 10,364,426 B1
(45) Date of Patent: Jul. 30, 2019

(54) PROCESS FOR REDUCING CELL DEATH AND INCREASING GROWTH OF AN ALGAL CULTURE

(71) Applicant: MISSING LINK TECHNOLOGY, LLC, Cypress, TX (US)

(72) Inventor: Samuel L. Shepherd, Cypress, TX (US)

(73) Assignee: MISSING LINK TECHNOLOGY, LLC, Cypress, TX (US)

( * ) Notice: Subject to any disclaimer, the term of this patent is extended or adjusted under 35 U.S.C. 154(b) by 113 days.

(21) Appl. No.: 15/449,043

(22) Filed: Mar. 3, 2017

(51) Int. Cl.
*C12N 13/00* (2006.01)
*C12M 1/00* (2006.01)
*C12M 1/06* (2006.01)

(52) U.S. Cl.
CPC ............. *C12N 13/00* (2013.01); *C12M 21/02* (2013.01); *C12M 23/58* (2013.01); *C12M 27/02* (2013.01); *C12M 29/04* (2013.01); *C12M 31/02* (2013.01)

(58) Field of Classification Search
CPC ...... C12M 21/02; C12M 23/04; C12M 31/06; C12M 29/06; C12M 41/00; C12M 43/02; C12M 43/08; C12M 23/08; C12M 23/26; C12M 31/02; C12M 41/08; C12M 41/18; C12M 43/06; C12M 21/04; C12M 23/58; C12M 31/10; C12M 41/48; C12M 43/04; B01D 53/85; B01D 2251/95; B01D 53/84; Y02A 50/2359; Y02A 50/2358; Y02A 90/26; C01C 1/04; C07C 1/04; C07C 67/02; C12N 1/12; E21B 43/16; Y02W 10/37; C12P 7/56; Y02E 50/343; Y02P 20/59; Y02P 60/24; A61K 2300/00; A61K 35/745; A61K 35/747; A61K 36/31; A61K 2236/19; A61K 31/202; A61K 31/26; A23L 19/00; A23L 1/296; A23L 33/105; A23L 33/135; A23L 33/30; A23L 33/40; A23V 2002/00; A23Y 2220/03; A23Y 2220/13; A23Y 2220/15; A23Y 2220/63; A23Y 2220/67; A23Y 2220/73; A23Y 2220/79; A23Y 2240/75; A23Y 2300/25; A23Y 2300/45; A23Y 2300/49; A23Y 2300/55; G06F 19/3475; A61B 8/08; A61N 7/00; C07K 14/435; C07K 14/47; C07K 7/56; G01N 33/5438; C02F 3/322

See application file for complete search history.

(56) References Cited

U.S. PATENT DOCUMENTS

| | | | |
|---|---|---|---|
| 4,069,149 A | 1/1978 | Jackson | |
| 4,286,066 A | 8/1981 | Butler et al. | |
| 5,688,674 A | 11/1997 | Choi et al. | |
| 6,599,735 B1 | 7/2003 | Bartok et al. | |
| 9,758,413 B1 * | 9/2017 | Shepherd | C02F 3/322 |
| 2002/0137187 A1 * | 9/2002 | Norsker | C12M 21/02 435/243 |
| 2007/0092962 A1 * | 4/2007 | Sheppard | C12M 21/02 435/266 |
| 2011/0068057 A1 * | 3/2011 | Haley, III | C02F 3/006 210/619 |
| 2013/0005022 A1 * | 1/2013 | Morris | C12M 21/02 435/257.1 |
| 2017/0096657 A1 * | 4/2017 | Gosselin | C02F 3/107 |

OTHER PUBLICATIONS

Sforza et al, "Adj. Light and Dark Cycles Can Optimize Photosyn. Efficiency in Algae. Growing in Photobioreactors", PLoS, Jun. 2012.*
Sforza et al "Adjusted Light and Dark Cycles Can Optimize Photosynthetic Efficiency in Algae Growing in Photobioreactors", PLoS One Peer-Review; Published Online Jun. 20, 2012; pp. 1-17. (Year: 2012).*

* cited by examiner

*Primary Examiner* — Deborah K Ware
(74) *Attorney, Agent, or Firm* — Egbert Law Offices, PLLC

(57) ABSTRACT

A process for reducing cell death in eukaryotic and prokaryotic organisms includes the steps of mixing the organisms with water in a first reactor, strobing light onto the mixture of organisms and water for a period of time, passing the strobed mixture into another reactor, and discharging the mixture from the another reactor. The step of strobing light includes strobing light to the mixture of organisms and water at a frequency of between 10 Hz and 40 Hz. The strobing of the light is between twenty flashes per second and eighty flashes per second. The first reactor is a continuously stirred reactor. The another reactor is a plug flow reactor. The organisms are in an algal culture.

6 Claims, 4 Drawing Sheets

PROCESS FOR REDUCING CELL DEATH AND INCREASING GROWTH OF AN ALGAL CULTURE

CROSS-REFERENCE TO RELATED APPLICATIONS

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present invention relates to the production of algal biomasses. More particularly, the present invention relates to processes for reducing cell death in such algal biomasses. In particular, the present invention relates to the use of strobe lights for the treating of algal biomasses.

2. Description of Related Art Including Information Disclosed Under 37 CFR 1.97 and 37 CFR 1.98

Algae fuel is a biofuel which is derived from algae. During photosynthesis, algae and other synthetic organisms capture carbon dioxide and sunlight and convert it into oxygen and biomass. Up to 99% of the carbon dioxide in solution can be converted in large scale open-pond systems. Several companies and government agencies are funding efforts to reduce capital and operating costs and make algae oil production commercially viable. The production of biofuels from algae does not reduce atmospheric carbon dioxide, because any carbon dioxide taken out the atmosphere by the algae is returned when the biofuels are burned. They do eliminate the introduction of new carbon dioxide by displacing fossil carbon fuels.

High oil prices and competing demands between foods and other biofuel sources and the world food crisis have ignited interest in algaculture (farming algae) so as to make vegetable oil, biodesiel, bioethanol, biogasoline, biomethanol, biobutanol and other biofuels by using land that is not suitable for agriculture. Among algal fuel's attractive characteristics is that it does not affect fresh water resources, can be produced using ocean and wastewater, and is biodegradable and relatively harmless to the environment if spilled. Algae can yield over thirty times more energy per unit area than other second-generation biofuel crops. The United States Department of Energy estimates that if algae replaced all petroleum fuel in the United States, it would require 15,000 square miles of land. This is less than one-seventh of the area of corn harvested in the United States.

Algae can produce up to 300 times more oil per acre than conventional crops, such as rapeseed, palms or soy beans. Since algae has a harvesting cycle of between one and ten days, it permits several harvests in a very short time period. Algae can be grown on land that is not suitable for other crops. This minimizes the issue of taking any pieces of land from the cultivation of food crops.

Most companies that are pursuing algae as a source of biofuels are pumping nutrient-laden waters through plastic tubes that are exposed to sunlight. Generally, the use of a photobioreactor is more difficult than an open pond and more costly. Another obstacle preventing widespread mass production of algae for biofuel production has been the equipment and structures needed to begin growing algae in large quantities. In closed loop systems, there is no problem of contamination by other organisms blown in by the air.

Algal market models indicate the development of fuels from algae will follow the pattern of crude oil from specialty to commodity chemical models of the 1920's and 1930's. The distinct difference is that during this period of time, the markets were required to be created, whereas today, the markets already exist.

Although "algal oil to transportation fuels" has been the driving force to date, only the co-products of algae oil production will bring economic stability to the market. As in the oil refining business, transportation fuel production alone is incapable of supporting the current cost of producing fuels due to the imbalance in supply and demand.

Each pound of algae produces about 0.4 pounds of algae protein meal, 0.2 pounds of carbohydrates, and 0.3 pounds of algae oil. Algae meal can be a major protein supplement used in aquatic, livestock and poultry feeds. As such, herd and flock numbers are major influences on algae meal consumption and prices. Algae products are and will be used to manufacture fuels, fuel feedstocks, foodstuffs, food products, and ethanol. Technical uses include adhesives, cleansing materials, polyesters, inks, coatings, polymers, detergents, quaternary salts, pharmaceuticals, chemical and biological feedstocks and other textiles.

The current demand for algal products is severely outpaced by the supply. It is not anticipated that supply will be capable of meeting demand for at least 15-20 years. Therefore, algal products will follow the classical specialty chemical models from current to at least ten years out. The transition from specialty to commodity will occur after that, first being noticed by variable market pricing swings from high to low.

As long as the demand outpaces supply, algal producers will continually pursue the "highest value" markets. These markets will consist of pharmaceuticals, plastics, nutraceuticals and specialty chemical feedstocks. As supply and demand come into balance, algal products will begin leaking over into the commodity models. Only then will the algal products be used in the transportation fuel markets. Once algae biomass becomes a commodity in the market, futures and options markets will develop. As such, there is a need for utilizing algae production so as to maximize the fuel output and to utilize the various components of the algae in an optimal and efficient manner.

It is known that algal biomasses is contain eukaryotic and prokaryotic cells. The peroxisomes, lysosomes, and microglia organelles are found in the eukaryotic and prokaryotic cells. These organelles contain enzymes that can oxidize certain proteins and fatty acids. The oxidation process produces hydrogen peroxide and proteins as a waste product in the cell. The hydrogen peroxide in the amyloid proteins are toxic to the cell due to its ability to react destructively with other cells and molecules. Peroxisomes also contain catalase enzymes that convert hydrogen peroxide to water and oxygen, thereby eliminating the toxicity.

Peroxisomes and lysosomes are also quite efficient at converting protein residuals that arise from cell death into basic amino acids that can be recycled directly into healthy cells. If peroxisome and lysosome activity is diminished, cell death becomes quite rapid in algal cultures. For example, it may take several days or weeks to generate an algal culture, only to lose the culture within hours due to what is commonly called a "crash". As such, a need has developed so as to treat the algal biomass so as to avoid the "crash".

Peroxisomes and lysosomes are roughly spherical in shape, bound by a single membrane, and are usually 0.5 to microns in diameter. There are several types in which the most common is the peroxisome. Peroxisomes derive their name from hydrogen peroxide, a reactive intermediate in the process of molecular breakdown that occurs in the micro body. Peroxisomes contain type II oxidizes, which are enzymes that use molecular oxygen in reactions to oxidize organic molecules. A product of these reactions is hydrogen peroxide, which is further metabolized in the water and oxygen by the enzyme catalase, a predominant constituent of peroxisomes. In addition, peroxisomes contain other enzyme systems that degrade various lipids. The algae glyoxysome is a peroxisome that also contains the enzymes of the glyoxylate cycle, which is crucial to the conversion of fat into carbohydrates.

In the past, various patents have been issued in the field of microorganisms growth and relating to processing bioharvests. For example, U.S. Pat. No. 6,599,735, issued on Jul. 29, 2003 to Bartok et al., describes a fermentation assembly comprising a vessel for culturing living cells, at least two storage flasks in fluid communication with the vessel for supply of liquids and a first transport means for transferring the liquids from the storage flasks to the vessel, individual appliances operably connected to the transport means for monitoring the supply of the contents of the storage flasks to the vessel, a harvest flask in fluid communication with the vessel and a second transport means for transferring the fermentation broth from the vessel to the harvest flask, and a device operably connected to the first transport means for controlling and maintaining a constant dilution rate in the vessel with varying rates of individual supply of liquid from the storage flasks to the vessel.

U.S. Pat. No. 5,688,674, issued on Nov. 18, 1997 to Choi et al., describes a metabolite, e.g., ethanol, that is continuously produced from low cost carbohydrate substrates by a process which comprises pulverizing the carbohydrate substrate, liquefying and saccharifying the pulverized substrate, continuously fermenting the lique-saccharified substrate in a fermentor equipped with a moving filter, in the presence of flocculent biological cells maintained at a concentration ranging from 90 to 160 grams/liter by using the moving filter and a culture medium to produce a fermentation product mixture, and recovering the desired metabolite from the fermentation product mixture.

U.S. Pat. No. 4,069,149, issued on Jan. 17, 1978 to Jackson, describes a deep-tank reactor utilized for fermentation of waste liquid or other liquid in a biological reaction resulting in a solid cellular material. The resulting solid material, which is in suspension, is initially separated from the bulk of the liquid by a gaseous flotation process, using the dissolved gas in the liquid as the source of gaseous bubbles for flotation purposes.

U.S. Pat. No. 4,286,066, issued on Aug. 25, 1981 to Butler et al., describes an apparatus for continuously fermenting a moist particulate feed and distilling the fermentation product where a pressure-locked auger forces a moist particulate feed from a hopper into a fermentation tank. Liquor is removed from the tank, and solids are separated therefrom, to produce a beer which is distilled in a distillation column. A combustion engine powers the auger and the means for separating solids, and the engine exhaust surrounds an inlet section of said auger to help heat the pressurized feed therein to produce fermentable sugar within the auger. The auger includes a section passing to the tank in heat exchange relation to the distillation column to provide heat for distillation. The column is a multistage column angled to face the sun and has an upper glass plate to allow solar radiation to enter and penetrate between the foraminous plates of the column.

It is an object of the present invention to provide a process and system that accelerates the mobility of eukaryotic and prokaryotic cells.

It is another object of the present invention to provide a process and system that improves the functionality of peroxisomes, lysosomes and microglia for the removal of hydrogen peroxide, protein and fatty acid accumulations within the eukaryotic and prokaryotic cells.

It is another object of the present invention to provide a system and process that enhances the ability to achieve optimal algal growth.

It is still another object of the present invention to provide a process and system which diminishes the crash rate of the algal culture.

These and other objects and advantages of the present invention will become apparent from a reading of the attached specification and appended claims.

BRIEF SUMMARY OF THE INVENTION

The present invention is a a process for reducing cell death in eukaryotic and prokaryotic organisms. The process comprises the steps of: (1) mixing the organisms with water in a first reactor; (2) strobing light onto the mixture of organisms and water for a period of time; (3) passing the strobed mixture into another reactor; and (4) discharging the mixture from the another reactor.

In the process of the present invention, light is strobed onto the mixture of organisms and water it at a frequency of between 10 Hz and 40 Hz and between twenty flashes per second and eighty flashes per second. Ideally, and preferably, the light is strobed onto the mixture of organisms and water at a frequency of 20 Hz and forty flashes per second. The light is strobed for sixteen hours on and eight hours off.

In the present invention, the first reactor is a continuously stirred reactor. The another reactor is a plug flow reactor. The strobed mixture flows by gravity from the continuously stirred reactor to the plug flow reactor. In the process of the present invention, the organisms are in an algal culture.

The process of the present invention can further include filtering contaminated water through a first filter so as to remove chemical oxygen demand, biological oxygen demand, and total suspended solids therefrom, introducing nutrients in a biomass into the interior of the first reactor, and passing the filtered contaminated water such that the filtrate containing phosphorus and nitrogen passes into the first reactor. The strobed mixture is reacted with carbon dioxide in the plug flow reactor. The reacted strobe mixture passes from the plug flow reactor to a filter. The mixture from the plug flow reactor is filtered so as to remove the algal biomass and to pass filtered water therefrom.

Nutrients are continuously circulated with the organisms in the first reactor. The circulating of the nutrients in the organisms is in a toroidal circulation pattern in a bottom-to-type pattern within the first reactor. The strobed mixture is discharged through a central drain of the first reactor such that the velocity of the strobe mixture is less than 2000 $N_{RE}$ (Reynolds Number) at the another reactor.

The present invention is also a system for reducing cell death in eukaryotic and prokaryotic organisms. This system comprises a first reactor adapted to receive the organisms therein, a strobe light directed toward an interior of the first reactor, and a second reactor in fluid communication with the first reactor such that the organisms flow by gravity from the first reactor to the second reactor. The first reactor is a continuously stirred reactor. The second reactor is a plug flow reactor. A power system is connected to the strobe light. Preferably, this power system is a 110 volt variable frequency drive power system. The light is strobed onto the mixture of organisms and water at a frequency of between 10 Hz and 40 Hz and between twenty flashes per second and eighty flashes per second. Preferably, the light is strobed onto the mixture in a frequency of 20 Hz and forty flashes per second. The first reactor has a stirring mechanism that causes a toroidal circulation pattern and a bottom-to-top circulation pattern of the organisms within the first reactor. The first reactor is a drain located centrally of the bottom of the first reactor.

This foregoing Section is intended to describe, with particularity, the preferred embodiments of the present invention. It is understood that modifications to these preferred embodiments can be made within the scope of the present invention. As such, this Section should not to be construed, in any way, as limiting of the broad scope of the present invention. The present invention should only be limited by the following claims and their legal equivalents.

DETAILED DESCRIPTION OF THE INVENTION

Figure 1:
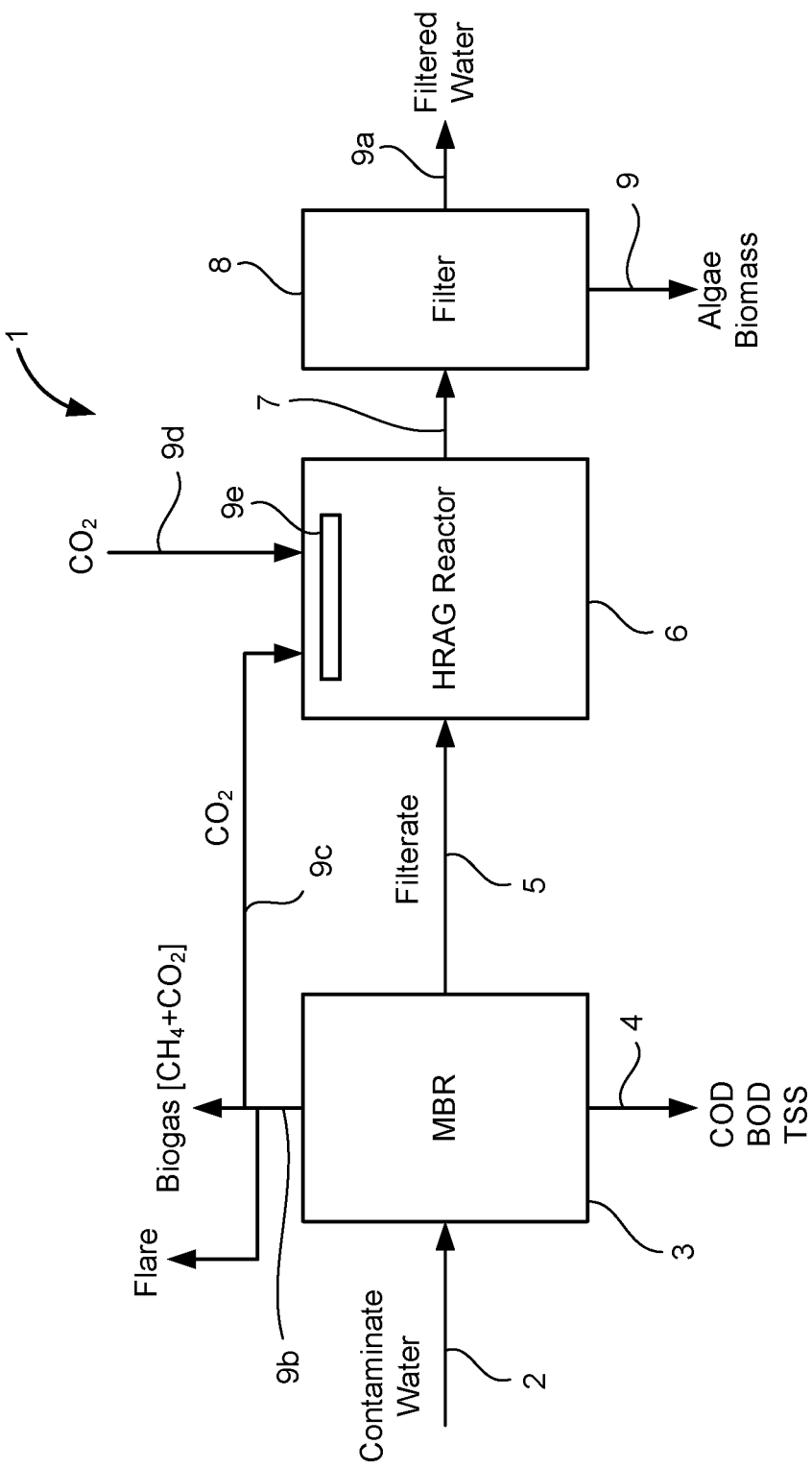
FIG. 1 is a flow diagram showing a process in accordance with the teachings of the preferred embodiment the present invention.

Referring to FIG. 1, there is shown the process and system 1 for the treatment of contaminated water. In particular, the contaminated water 2 enters the membrane biological reactor 3. The chemical oxygen demand (COD), the biological oxygen demand (BOD) and the total suspended solids (TSS) are shown as discharged through the outlet 4 of the membrane biological reactor. The filtrate 5 then passes from the membrane biological reactor 3 to the high rate algal growth reactor 6. The product of the reaction process in the high rate algal growth reactor 6 is an algal biomass which passes through the outlet 7 to a filter 8. Filter 8 serves to remove the algae through an outlet 9 and to pass filtered water 9a to an outlet thereof.

In FIG. 1, it can be seen that a biogas passes through an outlet 9b from the membrane biological reactor. This biogas can be flared, delivered to another location for energy use, or passed along line 9c to the high rate algal growth reactor 6. Carbon dioxide can be supplied along line 9d to the high rate algal growth reactor 6 so as to facilitate the reaction process in both the light and dark reactors associated with the high rate algal growth reactor 6.

In FIG. 1, it can be seen that the high-rate algal growth reactor 6 has strobe light 9e therein. The strobe light 9e is directed toward the interior of the reactor 6 so as to interact with a mixture of the eukaryotic and prokaryotic cells organisms therein. As will be described hereinafter, the use of the strobe light effectively reduces cell death in these eukaryotic and prokaryotic organisms. In particular, strobe light 9e increases peroxisome activity and diminishes the respiration (crash) rate in the algal culture with the reactor 6.

Figure 2:
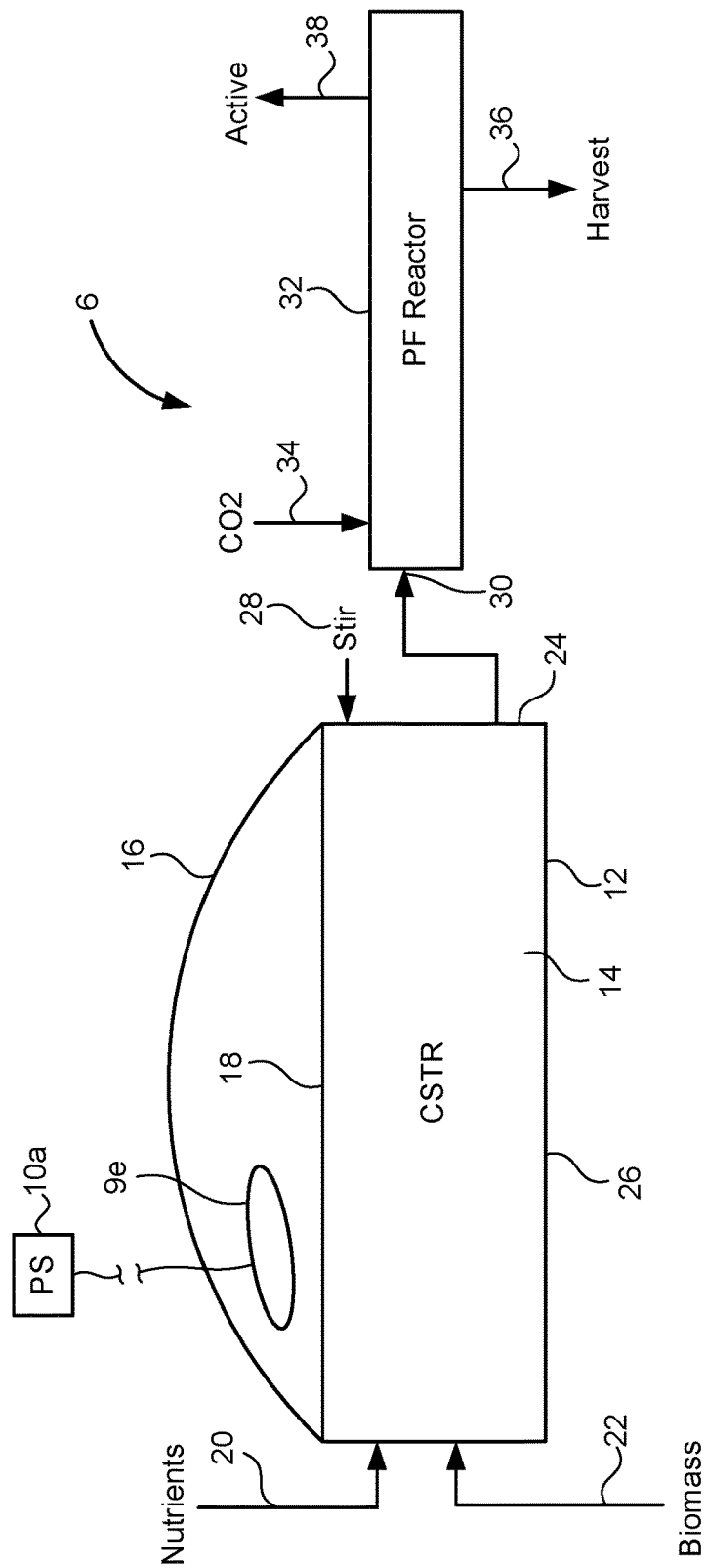
FIG. 2 is a block diagram showing a high-rate algal growth system in combination with a strobe light for growing microorganisms in accordance with the teachings of the present invention.

FIG. 2 is a detailed view of the high rate algal growth reactor 6. The high rate algal growth reactor 6 will include a continuously-stirred light tank reactor 12 and a dark plug flow reactor 32. The high rate algal growth system 6 is suitable for the growing of microorganisms and for the removal of phosphorus and nitrogen from the filtrate 5 of the membrane biological reactor 3. As was stated earlier, the membrane biological reactor 3 is extremely successful in removing COD, BOD and TSS. However, the filtrate of the membrane biological reactor 3 will include nitrogen and phosphorus. Fortunately, through the growth of algae in the high rate algal growth reactor 6, such nitrogen and phosphorus are removed by being used to facilitate the growth of algae.

In particular, the reactor 6 can be used for the growth of algae. The reactor 6 includes a continuously stirred tank reactor 12 having an interior volume 14. The continuously stirred tank reactor 12 is a light reactor. In other words, the microorganisms within the interior volume 14 of the continuously stirred tank reactor 12 are exposed to sunlight (or artificial light). There is an inflatable cover 16 that extends over the top 18 of the continuously stirred tank reactor 12. The cover 16 can be transparent so that the light can properly react with the microorganisms in the interior volume 14 of the continuously stirred tank reactor 12.

The continuously stirred tank reactor 12 includes inlets 20 and 22. Inlet 20 is intended to allow the filtrate 5 from the membrane biological reactor 3 to be introduced into the interior volume 14. Inlet 22 can be utilized so that a biomass can be introduced into the interior volume 14. Within the concept of the present invention, a single inlet can be utilized wherein the filtrate 5 and the biomass are mixed prior to being introduced to the interior volume 14. There is an outlet 24 located adjacent to the bottom 26 of the second container 14. Outlet 24 allows the grown microorganisms to be passed from the interior volume 14. A stirring mechanism 28 is cooperative with the interior volume 14 of the continuously stirred tank reactor 12 so as to continuously stir the microorganisms in the interior volume 14. In one embodiment, the stirring mechanism 28 can be an air bubbler cooperative with the microorganisms in the interior volume 14. Alternatively, the stirring mechanism 28 can be a liquid flow through the interior volume of the light reactor. The stirring mechanism 28 should create a toroidal circulation pattern of the microorganisms within the interior volume 14 of the continuously stirred tank reactor 12. Additionally, the stirring mechanism 28 should cause a bottom-to-top circulation pattern in the interior volume thereof.

Within the concept of the present invention, it should be noted that the phosphorus and nitrogen containing filtrate 5 and biomass can be introduced within the interior of the continuously stirred tank reactor 12. As such, the filtrate 5 and biomass can pass by way of a pipe extending into the interior volume 14 so as to be released downwardly into the interior volume 14. Similarly, the outlet 24 can be a pipe that extends into the interior volume 14 toward the center of the continuously stirred tank reactor 12. The outlet 24 can have an end opening within the interior volume 14 generally centrally of the continuously stirred tank reactor 12.

The outlet 24 is connected to the inlet 30 of the dark reactor 32. The dark reactor 32 is a plug flow reactor. Plug flow reactors, such as plug flow reactor 32, are used for chemical reactions in continuous flowing systems. Plug flow reactors are sometimes referred to as continuous tubular reactors. The fluid going through the plug flow reactor 32 flows through the reactor as a series of infinitely thin coherent "plugs", each with a uniform composition, traveling in the axial direction of the reactor, with each plug having a different composition from the ones before and after it. The key assumption is that as a plug flows through the plug flow reactor 32, the fluid is perfectly mixed in the radial direction but not in the axial direction (forwards or backwards). Each plug of differential volume is considered as a separate entity, effectively an infinitesimally small batch reactor, limiting to zero volume. As it flows through the plug flow reactor 32, the residence of the plug is a function of its position in the reactor.

Plug flow reactors are used for the chemical transformation of compounds as they are transported in systems resembling pipes. The "pipe" can represent a variety of engineered or natural conduits through which liquids or gases flow. An ideal plug flow reactor has a fixed residence time. Any fluid (plug) that enters the reactor at time t will exit the reactor at time t plus the residence time.

Referring to FIG. 2, the microorganisms from the continuously stirred tank reactor 12 pass into the inlet 30 of the plug flow reactor 32. The plug flow reactor 32 is maintained in a dark condition. Carbon dioxide 34 is introduced into the plug flow reactor 32 so as to allow the carbon dioxide to feed the microorganisms therein. Ultimately, a harvest 36 is taken from the bottom of the plug flow reactor 32. Any active culture that remains can pass along lines 38 outwardly of the plug flow reactor. As such, the plug flow reactor can operate as part of continuous process.

Importantly, in FIG. 2, the strobe light 9e is directed to the interior of the continuously stirred reactor 12. The strobe light 9e is connected to a power source 10a. Power source 10a is preferably a 110 volt variable frequency drive power source.

So as to demonstrate that the strobe light 9e increases peroxisome activity and diminishes the respiration (crash) rate in the algal culture, an experiment was conducted using four light sources. In particular, strobe 1 is a 10 Hz twenty flashes per second strobe light. Strobe 2 was a 20 Hz and forty flashes per second strobe light. Strobe three is a 40 Hz and eighty flashes per second strobe light. Strobe 4 is a 80 Hz and one-hundred and sixty flashes per second strobe light. The strobes were connected to a 110 volt variable frequency drive. A series of three cultures per strobe experiment were established using an identical nutrient medium consisting of 110 milliliter beakers containing 18.0 g $NaHCO_3$, 2.52 g $NaNO_3$, 0.5 g $K_2HPO_4$, 1.0 g $K_2SO_4$, 0.04 g $CaCl_2$, 0.08 g $Na_2EDTA$, 0.02 g $MgSO_4$ $7H_2O$, 0.01 g $FeSO_4$ $7H_2O$. The experiments were conducted over a thirty day period with exposure to light for sixteen hours on and eight hours off. The chlorophyll A was measured daily along with pH and temperature. Averages of each of these three cultures were calculated and compiled in the following table:

|        |      | DAYS |      |      |      |       |       |       |
|--------|------|------|------|------|------|-------|-------|-------|
| STROBE |      | 1    | 2    | 3    | 4    | 5     | 6     | 7     |
| 1      | pH   | 8.3  | 8.4  | 8.6  | 8.7  | 8.9   | 8.9   | 9     |
|        | Temp | 90   | 90   | 90   | 90   | 90    | 90    | 90    |
|        | ChlA | 2208 | 2892 | 4863 | 6603 | 15943 | 27889 | 48873 |
| 2      | pH   | 8.3  | 8.4  | 8.5  | 8.6  | 8.6   | 8.8   | 9     |
|        | Temp | 90   | 90   | 90   | 90   | 90    | 90    | 90    |
|        | ChlA | 2104 | 2736 | 4902 | 6206 | 12508 | 29625 | 43570 |
| 3      | pH   | 8.4  | 8.4  | 8.4  | 8.6  | 8.9   | 8.9   | 9     |
|        | Temp | 90   | 90   | 90   | 90   | 90    | 90    | 90    |
|        | ChlA | 2218 | 2882 | 4788 | 6839 | 15934 | 28903 | 49421 |
| 4      | pH   | 8.3  | 8.4  | 8.6  | 8.6  | 8.6   | 8.9   | 8.9   |
|        | Temp | 90   | 90   | 90   | 90   | 90    | 90    | 90    |
|        | ChlA | 2232 | 2904 | 4907 | 6558 | 14982 | 29314 | 48703 |

|        |      | DAYS  |        |        |        |        |        |        |
|--------|------|-------|--------|--------|--------|--------|--------|--------|
| STROBE |      | 8     | 9      | 10     | 11     | 12     | 13     | 14     |
| 1      | pH   | 9.2   | 8.7    | 9.2    | 9      | 9.3    | 9.2    | 9      |
|        | Temp | 90    | 90     | 90     | 90     | 90     | 90     | 90     |
|        | ChlA | 88302 | 147873 | 158345 | 149042 | 148567 | 147828 | 149342 |
| 2      | pH   | 9.2   | 8.7    | 9.2    | 9      | 9.3    | 9.2    | 9      |
|        | Temp | 90    | 90     | 90     | 90     | 90     | 90     | 90     |
|        | ChlA | 84967 | 125709 | 162715 | 166815 | 168357 | 166429 | 167902 |
| 3      | pH   | 9.2   | 8.7    | 9.2    | 9      | 9.3    | 9.2    | 9.1    |
|        | Temp | 90    | 90     | 90     | 90     | 90     | 90     | 90     |
|        | ChlA | 77903 | 142619 | 148729 | 152482 | 155746 | 150821 | 148201 |
| 4      | pH   | 8.9   | 9      | 9.2    | 8.7    | 9.2    | 9      | 9.3    |

| | | -continued | | | | | | |
|---|---|---|---|---|---|---|---|---|
| | Temp | 90 | 90 | 90 | 90 | 90 | 90 | 90 |
| | ChlA | 82690 | 151780 | 162098 | 166402 | 163059 | 158451 | 157182 |

| | | DAYS | | | | | | |
|---|---|---|---|---|---|---|---|---|
| STROBE | | 15 | 16 | 17 | 18 | 19 | 20 | 21 |
| 1 | pH | 8.7 | 8.3 | 8.3 | 8 | 7.2 | 7 | 7.1 |
| | Temp | 90 | 90 | 90 | 90 | 90 | 90 | 90 |
| | ChlA | 151409 | 144390 | 146341 | 74841 | 38253 | 32582 | 27602 |
| 2 | pH | 9 | 9.2 | 8.7 | 9.2 | 9 | 9.3 | 9.2 |
| | Temp | 90 | 90 | 90 | 90 | 90 | 90 | 90 |
| | ChlA | 162583 | 166823 | 158293 | 144078 | 137639 | 138470 | 124832 |
| 3 | pH | 8.8 | 8.1 | 8 | 8.1 | 7.7 | 7.6 | 7.3 |
| | Temp | 90 | 90 | 90 | 90 | 90 | 90 | 90 |
| | ChlA | 147328 | 137821 | 110842 | 82741 | 47529 | 30832 | 28880 |
| 4 | pH | 9.2 | 9 | 8.7 | 8.3 | 8.3 | 8 | 7.2 |
| | Temp | 90 | 90 | 90 | 90 | 90 | 90 | 90 |
| | ChlA | 152301 | 149026 | 88206 | 29033 | 21049 | 12933 | 16050 |

As can be seen from the above Table, strobes 1, 3 and 4 all behave statistically identical. Strobe 2, on the other hand, operating an electrical AC frequency of 20 Hz and forty flashes per second delays the onset of algal culture clash. The pH of each trial shows a decrease in pH as the chlorophyll A concentrations declined. It is clear that the pH remains elevated with strobe number 2. As such, as result of this test, it is clear that the optimal frequency of 20 Hz and forty flashes per second is reserved for eukaryotic and prokaryotic cells to increase the mobility and functionality of peroxisomes, lysosomes and microglia for the removal of hydrogen peroxide, protein and fatty acid accumulations within the cell. The eukaryotic and prokaryotic cell (respiration) is promoted by an accumulation of protein, fatty acids and other organic debris during the growth phase of the cell. The organic debris including the proteins, enzymes, and fatty acids tend to accumulate on the live cell membranes so as to cause a lack of nutrient transport across the cell membrane, resulting in cell death. This process becomes "auto-accelerating" so as to result in an exponentially increasing rate of respiration (cell death). As such, in the present invention, by applying the light from the strobe light 9e, the present invention is able to reduce cell death and to accelerate the mobility and functionality of the peroxisomes, lysosomes and microglia for the removal of hydrogen peroxide, protein and fatty acid accumulations within the cell.

Figure 3:
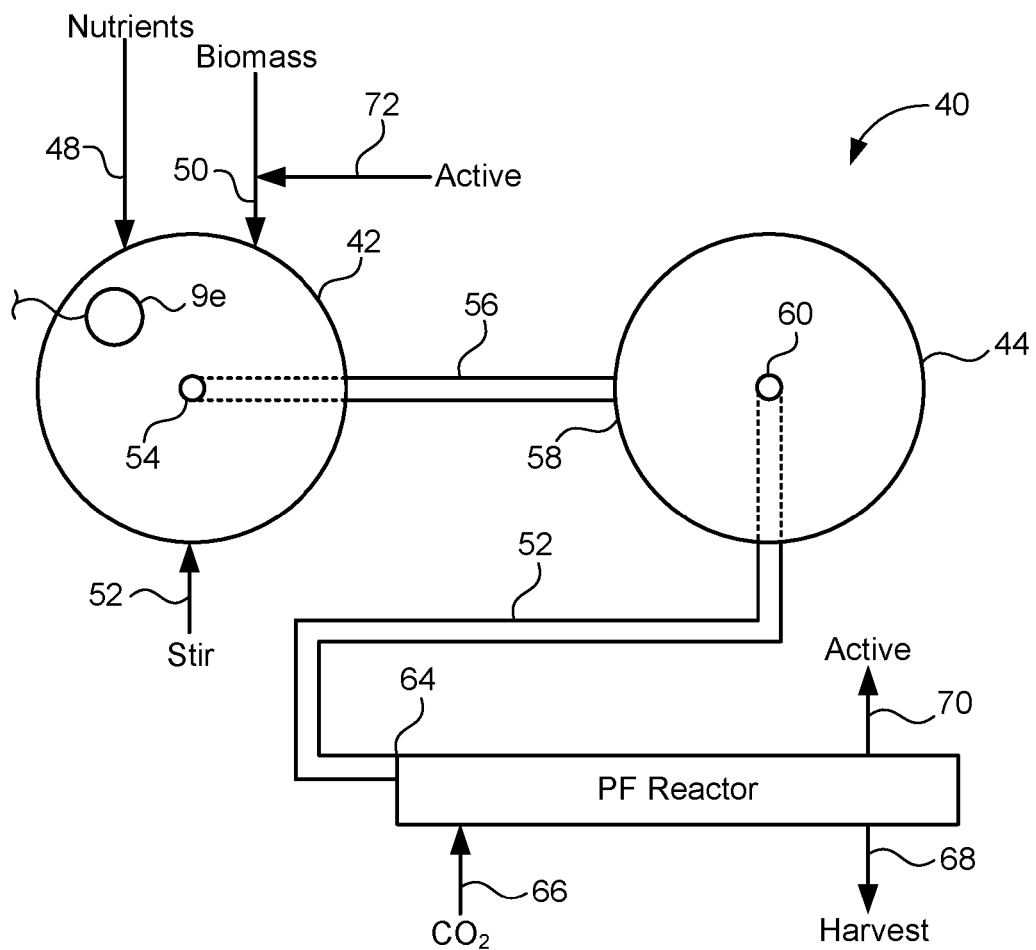
FIG. 3 is a diagrammatic illustration showing the high-rate algal growth system for growing microorganisms in accordance with the teachings of the present invention.

FIG. 3 shows an alternative embodiment of the system 40 of the present invention. The system 40 includes a first light reactor 42, a second light reactor 44, and a plug flow reactor 46. The first reactor 42 has an inlet 48 and a biomass inlet 50. These inlets 48 and 50 can be separate inlets or they can be as a single combined inlet. The stirring mechanism 52 serves to create the toroidal circulation pattern and the bottom-to-top circulation pattern. The outlet 54 of the first reactor 42 is located centrally of the reactor 42. Outlet 54 will flow through pipe 56 so as to enter the second reactor 44 at inlet 58. The second reactor 44 is also a light reactor configured so as to further treat the microorganisms from the first reactor 42. The second reactor 44 also has an outlet 60 which allows the microorganisms therein to pass along pipe 62 to the inlet 64 of the plug flow reactor 46. Carbon dioxide 66 is mixed with the microorganisms in the plug flow reactor 46. As a result, the harvested microorganisms 68 would be removed from the bottom of the plug flow reactor 46. The active culture 70 can be released from the plug flow reactor so as to pass as an active culture along line 72 to the biomass inlet 50. The strobe light 9e is shown as positioned within the continuously stirred reactor 42.

Figure 4:
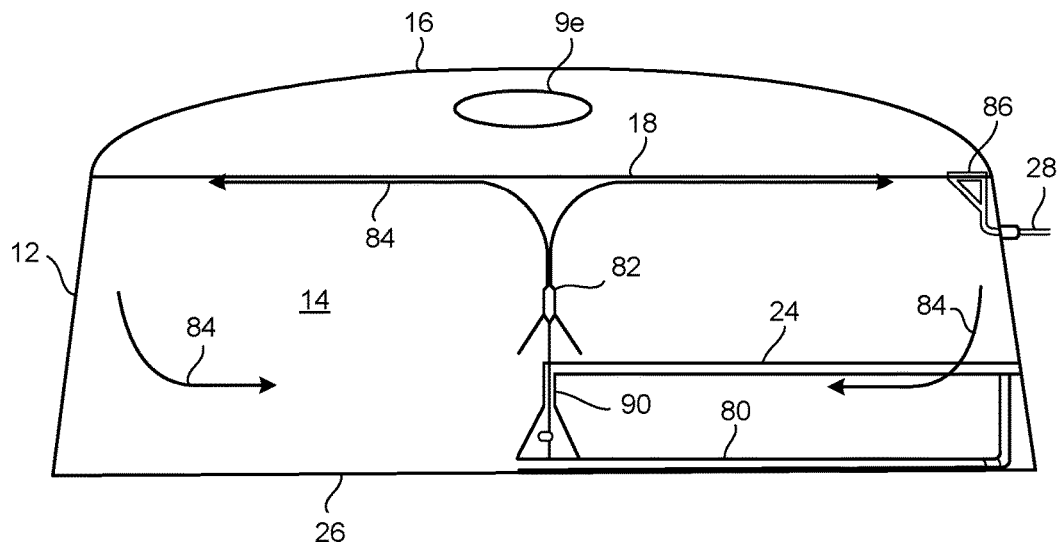
FIG. 4 is across-sectional view showing the bottom-to-top circulation pattern of the microorganisms within the continuously stirred reactor.

FIG. 4 is a side view of the continuously stirred tank reactor 12. The continuously stirred tank reactor 12 has interior volume 14. An inflatable cover 16 extends over the top of the continuously stirred tank reactor 12.

In FIG. 4, it can be seen that the nutrients and biomass are introduced through the inlet 80 which extends through the interior volume 14 generally adjacent to the bottom 26 of the continuously stirred tank reactor 12. Ultimately, the biomass and nutrients are released through the outlet 82 so as to flow upwardly toward the top 18 of the continuously stirred tank reactor 12. As can be seen by arrow 84, the biomass and nutrients flow upwardly in a bottom-to-top pattern. A skimmer 86 can be located adjacent to the top 18 of the continuously stirred tank reactor 12 so as to skim the surface of the microorganisms within the interior volume 14. The stirring mechanism 28 is provided so as to create the proper toroidal circulation pattern within the interior volume 14. The stirring mechanism 28 can be in the form of an air bubbler or a nozzle for creating a liquid flow therein.

The outlet 24 is illustrated as having an opening 90 generally centrally of the interior volume 14. As such, the reacted nutrients and microorganisms of the sunlight can flow outwardly through the outlet 28 toward the dark reactor.

Figure 5:
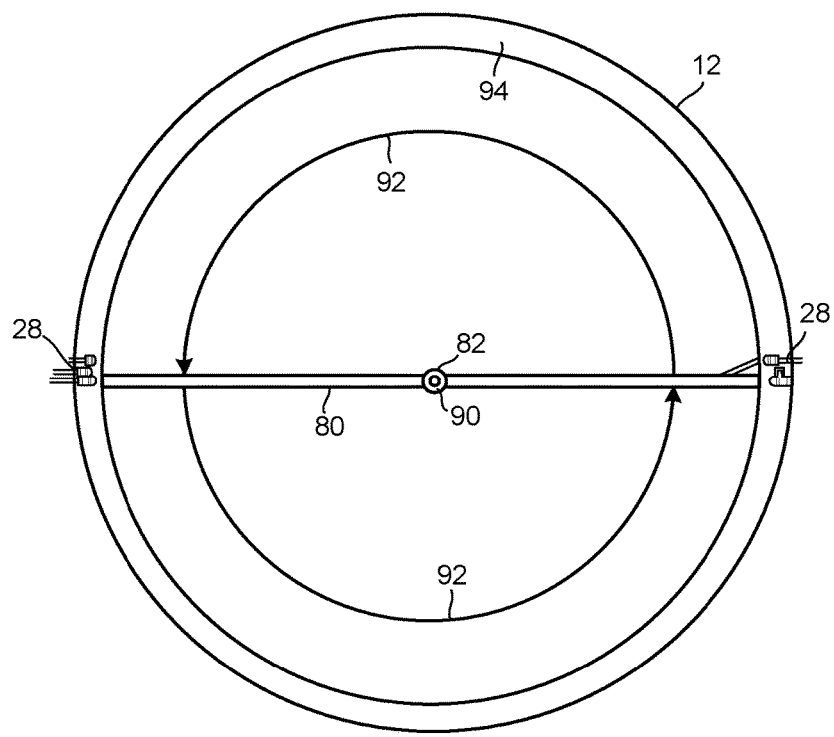
FIG. 5 is a plan view showing the toroidal circulation pattern of the microorganisms within the continuously stirred reactor.

FIG. 5 illustrates the toroidal circulation pattern (illustrated by arrows 92). In particular, the nutrients are introduced centrally by pipe 80 of the inlet 82. The outlet opening 90 is also positioned centrally of the continuously stirred tank reactor 12. The stirring mechanism 28 is illustrated as located at opposite sides of the continuously stirred tank reactor 12. Various configurations of stirring mechanisms can be incorporated within the concept of the present invention.

In FIG. 5, it can be seen that the continuously stirred tank reactor 12 has a wall 94 extending therearound. The continuously stirred tank reactor 12 will, in the preferred embodiment of the present invention, have a depth of less than ten feet. The walls 94 can be suitably flexible so as to be easily positioned in any desired location with a minimal weight and footprint.

The algae growth system of the present invention incorporates the properties of the photosynthesis reactions known as the "light reaction" and the "dark reaction." The overall reaction rate kinetics is described as oscillating between the zeroth order and first order. The conversion of carbon dioxide into carbohydrates is well understood, but the optimal reactor configuration has not, until now, been determined.

The reaction process for algal growth is known as autocatalytic. This autocatalytic behavior of algal growth is represented by a sequence of events. The events are described below as follows. The overall process of photosynthesis takes place in four stages, including light dependent reactions and dark reactions. The light dependent reactions include stages 1-3 of the autocatalytic behavior of algal growth. Stage 1 is the energy transfer in antenna chlorophyll which takes place in the femtosecond (1 femtosecond (fs)=$10^{-15}$ s) to picosecond (1 picosecond (ps)=$10^{-12}$ s) time scale. Stage 2 is the transfer of electrons in photochemical reactions, which takes place in the picosecond to nanosecond time scale (1 nanosecond (ns)=$10^{-9}$ s). Stage 3 is the electron transport chain and ATP synthesis, which takes place on the microsecond (1 microsecond (μs)=10's) to millisecond (1 millisecond (ms)=10's) time scale. The dark reaction (Calvin Cycle) includes stage 4 of the autocatalytic behavior of algal growth. Stage 4 is the carbon fixation and export of stable products and takes place in the millisecond to second time scale. The first three stages occur in the thylakoid membranes.

The present invention incorporates the uniqueness of establishing the first three stages in the "light" continuous stirred tank reactor 12 followed by the "dark" reaction fourth stage in a plug flow reactor 32 to complete the algal growth and carbon dioxide fixation. This configuration allows for growth rates exceeding 120 grams/m²/day. To date, no other technology has been able to incorporate the optimal reactor configuration to algal growth.

The light reactor system may be comprised of one or more light reactors 12 in series to maximize the light absorption. The algal biomass removed via the drain of each light reactor is directed to the successive light reactor 10 or to the dark plug flow reactor 32. The material enters the dark plug flow reactor where the fluid velocity is decreased to achieve an $N_{Re}$ (Reynolds Number) of less than 2000. The algal biomass in the plug flow reactor is deprived of light, but supplied with carbon dioxide as required to maintain the Calvin cycle conversion to sugars. The plug flow reactor is so configured as to allow the algae to settle to the bottom for harvest while maintaining an active culture that is returned to the light reactors.

This reactor configuration will result in algal growth rates exceeding 120 grams/m²/day with solar energy inputs of greater than 120 watts per square meter.

The foregoing disclosure and description of the invention is illustrative and explanatory thereof. The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

I claim:

1. A process for reducing cell death and increasing growth of an algal culture, the process comprising:
   mixing the algal culture with water in a first reactor, the first reactor being a continuously stirred reactor, the step of mixing comprising:
      continually circulating nutrients and the algal culture in a toroidal pattern and in a bottom-to-top pattern within said first reactor;
   strobing light onto the mixture of algal culture and water for a period of time at a frequency of between 10 Hz and 40 Hz and between twenty flashes per second and eighty flashes per second;
   flowing the strobed mixture of the algal culture and water from said first reactor for a period of time to a second reactor, the second reactor being a plug flow reactor, the step of flowing further comprising:
      discharging the strobed mixture through a central drain of the first reactor to decrease fluid velocity of the strobed mixture and obtain a Reynolds Number ($N_{RE}$) of less than 2000 is the second reactor;
   discharging the strobed mixture from the second reactor; and
   reducing cell death and increasing growth of said algal culture at a growth rate exceeding 120 grams/m²/day.

2. The process of claim 1, the step of strobing light comprising:
   strobing light onto the mixture of the algal culture and the water at a frequency of 20 Hz and forty flashes per second.

3. The process of claim 1, the step of strobing light comprising:
   strobing the light for sixteen hours on and eight hours off.

4. The process of claim 1, further comprising:
   filtering contaminated water through a first filter so as to remove chemical oxygen demand, biological oxygen demand and total suspended solids therefrom;
   introducing nutrients in a biomass into an interior of said first reactor; and
   passing the filtered contaminated water such that a filtrate containing phosphorus and nitrogen passes into the first reactor.

5. The process of claim 4, further comprising:
   reacting the strobed mixture with carbon dioxide in the second reactor; and
   passing the reactive strobed mixture from the second reactor to the first filter.

6. The process of claim 5, further comprising:
   filtering the mixture from the second reactor so as to remove the algal biomass and to pass filtered water therefrom.

* * * * *